US010758472B2

(12) United States Patent
Zaidel et al.

(10) Patent No.: US 10,758,472 B2
(45) Date of Patent: *Sep. 1, 2020

(54) ORAL CARE COMPOSITION WITH CROSS-LINKED POLYMER PEROXIDE

(71) Applicant: COLGATE-PALMOLIVE COMPANY, New York, NY (US)

(72) Inventors: Lynette Zaidel, Cranford, NJ (US); Guisheng Pan, Philadelphia, PA (US); Suman Chopra, Monroe, NJ (US); Prakasarao Mandadi, Flemington, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/900,346

(22) Filed: Feb. 20, 2018

(65) Prior Publication Data

US 2018/0333346 A1 Nov. 22, 2018

Related U.S. Application Data

(63) Continuation of application No. 15/344,504, filed on Nov. 4, 2016, now Pat. No. 9,895,304, which is a continuation of application No. 14/723,139, filed on May 27, 2015, now Pat. No. 9,517,194, which is a continuation of application No. 10/929,087, filed on Aug. 27, 2004, now abandoned.

(51) Int. Cl.
*A61K 8/00* (2006.01)
*A61K 8/81* (2006.01)
*A61K 8/02* (2006.01)
*A61K 8/22* (2006.01)
*A61Q 11/00* (2006.01)
*A61Q 11/02* (2006.01)
*A61K 8/24* (2006.01)
*A61K 8/90* (2006.01)
*A61K 8/49* (2006.01)
*A61K 8/891* (2006.01)

(52) U.S. Cl.
CPC .......... *A61K 8/8176* (2013.01); *A61K 8/0208* (2013.01); *A61K 8/22* (2013.01); *A61K 8/24* (2013.01); *A61K 8/49* (2013.01); *A61K 8/817* (2013.01); *A61K 8/891* (2013.01); *A61K 8/90* (2013.01); *A61Q 11/00* (2013.01); *A61Q 11/02* (2013.01); *A61K 2800/805* (2013.01)

(58) Field of Classification Search
CPC combination set(s) only.
See application file for complete search history.

(56) References Cited

U.S. PATENT DOCUMENTS

| 2,667,473 | A |  | 1/1954 | Morner et al. |
| 2,938,017 | A |  | 5/1960 | Grosser |
| 2,947,633 | A |  | 8/1960 | Perry et al. |
| 3,277,066 | A |  | 10/1966 | Grosser et al. |
| 3,306,881 | A |  | 2/1967 | Grosser et al. |
| 3,306,886 | A |  | 2/1967 | Grosser et al. |
| 3,759,880 | A |  | 9/1973 | Hoffmann et al. |
| 3,934,000 | A |  | 1/1976 | Barth |
| 3,992,562 | A |  | 11/1976 | Denzinger et al. |
| 4,013,825 | A |  | 3/1977 | Denzinger et al. |
| 4,032,627 | A |  | 6/1977 | Suchan et al. |
| 4,038,257 | A |  | 7/1977 | Suzuki et al. |
| 4,136,250 | A |  | 1/1979 | Mueller et al. |
| 4,224,427 | A |  | 9/1980 | Mueller et al. |
| 4,250,322 | A |  | 2/1981 | Efimov et al. |
| 4,276,402 | A |  | 6/1981 | Chromecek et al. |
| 4,277,595 | A |  | 7/1981 | Deichert et al. |
| 4,341,889 | A |  | 7/1982 | Deichert et al. |
| 4,423,099 | A |  | 12/1983 | Mueller et al. |
| 4,543,398 | A |  | 9/1985 | Bany et al. |
| 4,564,514 | A |  | 1/1986 | Drauz et al. |
| 5,008,106 | A | * | 4/1991 | Merianos ............... A01N 59/00 424/78.06 |
| 5,077,047 | A |  | 12/1991 | Biss et al. |

(Continued)

FOREIGN PATENT DOCUMENTS

CA 2028354 5/1991
CA 210778 11/1992

(Continued)

OTHER PUBLICATIONS

International Specialty Products, 2003, "Applications—Toothpaste and Mouthwash," ISP Polymers for Oral Care, 10 pgs.
International Specialty Products, 2003, "Product and Applications Guide," ISP Polymers for Oral Care, 19 pgs.
Porras et al., 2004, "Studies of formation of W/O nano-emulsions," Colloids and Surfaces A 249:115-118.
Prosecution History from U.S. Appl. No. 10/929,087, to Nov. 10, 2011.
Prosecution History from U.S. Appl. No. 11/285,871 to Aug. 30, 2011.

(Continued)

*Primary Examiner* — Banjamin J Packard

(57) ABSTRACT

Oral care compositions comprising:
(a) a peroxide complex comprising a peroxide component and an N-vinyl heterocyclic polymer (e.g., poly-N-vinyl polylactam, or poly-N-vinyl-polyimide);
(b) a whitening agent (e.g., hydrogen peroxide); and
(c) an orally acceptable carrier.
In one embodiment, the carrier comprises a film forming material. Methods are also provided for making an oral care composition comprising:
(a) mixing a whitening agent, silicone adhesive and carrier fluid to form a homogenous mixture;
(b) adding a peroxide complex to said homogenous mixture, wherein said complex comprises hydrogen peroxide and an N-vinyl heterocyclic polymer; and
(c) mixing under vacuum.

12 Claims, No Drawings

(56) References Cited

U.S. PATENT DOCUMENTS

| | | | |
|---|---|---|---|
| 5,108,742 A * | 4/1992 | Merianos | A61K 8/22 424/401 |
| 5,130,124 A | 7/1992 | Merianos et al. | |
| 5,310,563 A | 5/1994 | Curtis et al. | |
| 5,312,619 A | 5/1994 | Shih et al. | |
| 5,425,953 A | 6/1995 | Sintov et al. | |
| 5,453,284 A * | 9/1995 | Pellico | A61K 8/66 424/49 |
| 5,709,852 A * | 1/1998 | Gopalkrishnan | A61K 8/90 424/401 |
| 5,718,886 A | 2/1998 | Pellico | |
| 5,766,574 A | 6/1998 | Christina-Beck et al. | |
| 5,776,435 A | 7/1998 | Gaffar et al. | |
| 5,820,853 A * | 10/1998 | Glandorf | A61K 8/02 424/52 |
| 5,945,032 A * | 8/1999 | Breitenbach | A01N 59/00 252/186.29 |
| 5,955,552 A | 9/1999 | Sojka | |
| 6,083,421 A | 7/2000 | Huang et al. | |
| 6,086,856 A | 7/2000 | Saferstein | |
| 6,106,812 A | 8/2000 | Prencipe et al. | |
| 6,228,385 B1 | 5/2001 | Shick | |
| 6,231,848 B1 | 5/2001 | Breitenbach et al. | |
| 6,290,933 B1 | 9/2001 | Durga et al. | |
| 6,387,392 B1 | 5/2002 | Saito et al. | |
| 6,387,995 B1 | 5/2002 | Sojka | |
| 6,447,757 B1 | 9/2002 | Orlowski et al. | |
| 6,514,484 B2 | 2/2003 | Rajaiah et al. | |
| 6,514,543 B2 | 2/2003 | Montgomery | |
| 6,555,020 B1 | 4/2003 | Chadwick et al. | |
| 6,685,921 B2 | 2/2004 | Lawlor | |
| 7,118,732 B2 | 10/2006 | Ibrahim et al. | |
| 9,517,194 B2 | 12/2016 | Zaidel | A61K 8/0208 |
| 2002/0122776 A1 | 9/2002 | Joiner et al. | |
| 2002/0137728 A1 | 9/2002 | Montgomery | A61K 8/02 514/99 |
| 2003/0124065 A1 | 7/2003 | Majeti et al. | |
| 2003/0124067 A1 * | 7/2003 | Yue | A61K 8/19 424/52 |
| 2003/0133884 A1 | 7/2003 | Chang | |
| 2003/0152528 A1 | 8/2003 | Singh et al. | |
| 2003/0198604 A1 | 10/2003 | Lawlor | |
| 2003/0206874 A1 | 11/2003 | Doyle et al. | |
| 2003/0228339 A1 | 12/2003 | El-nokaly et al. | |
| 2003/0235549 A1 | 12/2003 | Singh et al. | |
| 2004/0024110 A1 | 2/2004 | Hamersky et al. | |
| 2004/0086468 A1 | 5/2004 | Prosise et al. | |
| 2004/0241110 A1 | 12/2004 | Lee | |
| 2005/0008584 A1 | 1/2005 | Montgomery | |
| 2005/0036956 A1 | 2/2005 | Fei et al. | |
| 2005/0038181 A1 | 2/2005 | Chopra et al. | |
| 2005/0069502 A1 | 3/2005 | Chopra et al. | |
| 2005/0249678 A1 | 11/2005 | Hassan et al. | |
| 2005/0249679 A1 | 11/2005 | Cameron et al. | |
| 2005/0281757 A1 | 12/2005 | Ibrahim et al. | |
| 2006/0045854 A1 | 3/2006 | Zaidel et al. | |
| 2007/0253916 A1 | 11/2007 | Maitra et al. | |

FOREIGN PATENT DOCUMENTS

| | | |
|---|---|---|
| DE | 2365631 | 10/1975 |
| DE | 2542314 | 4/1976 |
| DE | 3034505 | 3/1981 |
| EP | 0417971 | 3/1991 |
| FR | 2465236 | 3/1981 |
| GB | 1205325 | 9/1970 |
| GB | 1433715 | 4/1976 |
| GB | 1443715 | 7/1976 |
| JP | S60-233110 | 11/1985 |
| JP | S61-009424 | 1/1986 |
| JP | S61-030566 | 2/1986 |
| JP | H10-030566 | 2/1998 |
| JP | H10-305666 | 11/1998 |
| TW | 200621299 | 7/2006 |
| WO | WO 91/007184 | 5/1991 |
| WO | WO 00/026424 | 5/2000 |
| WO | WO 01/051012 | 7/2001 |
| WO | WO 02/072050 | 9/2002 |
| WO | WO 02/074274 | 9/2002 |
| WO | WO 04/016237 | 2/2004 |
| WO | WO 05/018591 | 3/2005 |
| WO | WO 05/070378 | 8/2005 |
| WO | WO 05/097053 | 10/2005 |
| WO | WO 06/026424 | 3/2006 |
| WO | WO 06/073822 | 7/2006 |

OTHER PUBLICATIONS

Prosecution History from U.S. Appl. No. 11/739,393, now published as U.S. Publication No. 2007/0253916 on Nov. 1, 2007.

Spindler et al., 2002, "Poly-Pore® microparticle delivery system, a multifuntional delivery system for personal care products," Cosmetics and Toiletries Manufacture Worldwide, 4 pgs.

* cited by examiner

ORAL CARE COMPOSITION WITH CROSS-LINKED POLYMER PEROXIDE

CROSS-REFERENCE TO RELATED APPLICATIONS

This application is a continuation of U.S. patent application Ser. No. 15/344,504, filed Nov. 4, 2016, which is a continuation of U.S. patent application Ser. No. 14/723,139, now U.S. Pat. No. 9,517,194, which is a continuation of U.S. patent application Ser. No. 10/929,087, filed Aug. 27, 2004, which is abandoned; the entireties of which are hereby incorporated herein by reference.

INTRODUCTION

The present invention relates to oral care compositions and methods. In particular, the present invention includes compositions and methods for whitening of teeth.

Many individuals desire a "bright" smile and white teeth, and consider dull and stained teeth cosmetically unattractive. Unfortunately, Without preventive or remedial measures, stained teeth are almost inevitable due to the absorbent nature of dental material. Everyday activities such as smoking or other oral use of tobacco products, and eating, chewing or drinking certain foods and beverages (in particular coffee, tea and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-whim color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function or utility of present invention, it is believed that this porous nature of the enamel is where discoloring substances permeate the enamel and discolor the teeth.

There are a variety of compositions described in the art for preventing or treating the discoloration of teeth. In particular, to combat staining and brighten or restore the natural enamel color, a variety of products containing bleaching materials are commercially available for professional and consumer use. The most commonly accepted chemicals used in teeth whitening today are peroxides. Peroxides are generally deemed safe from a physiological standpoint, and can be effective to whiten teeth. Such peroxides include hydrogen peroxide, carbamide peroxide, sodium perborate, and sodium percarbonate. When these peroxides are in appropriate contact with teeth they will usually oxidize stains, rendering the teeth whiter.

Professional dental treatments frequently include a tooth surface preparation such as acid etching followed by the application of highly concentrated bleaching solutions (e.g., up to 37% hydrogen peroxide) and/or the application of heat or light. (See, e.g., U.S. Pat. Nos. 5,425,953 and 5,766,574.) These procedures provide rapid results, but are expensive, and often require several trips to the dentist. In many cases, the patient's lips are uncomfortably retracted during the entire treatment and the patient is confined to sitting in the dental chair.

Alternatively, at home bleaching systems can be used. These systems have gained significant popularity in the past decade because of reduced cost, and increased convenience. Instead of time consuming and frequent trips to the dentist, the tooth whitener is purchased at a consumer retail store and may be used while performing other personal tasks or errands, relaxing or sleeping.

Current home treatment methods include abrasive toothpastes, toothpastes that produce oxides, whitening gels for use with a dental tray and whitening strips. The effectiveness of such techniques depends on a variety of factors including the type and intensity of the stain, the type of bleaching agent, contact time of the bleaching agent on the teeth, the amount of available bleaching active in the composition, the ability of the bleaching agent to penetrate the tooth enamel, and consumer compliance. Effectiveness is also dependant on the amount of bleaching active in the composition, the ability of the active to be released during use, and the stability of the active in the product. However, the effectiveness of many of these treatments is adversely affected because of deficiencies in one or more factors relating to the composition and consumer compliance.

SUMMARY

The present invention provides oral care compositions. Embodiments include oral care compositions comprising:
 (a) a peroxide complex comprising a peroxide component and an N-vinyl heterocyclic polymer;
 (b) a whitening, agent; and
 (c) an orally acceptable carrier.

In various embodiments, the N-vinyl heterocyclic polymer comprises a polymer selected from the group consisting of poly-N-vinyl polylactams, poly-N-vinyl-polyimides and mixtures thereof. In one embodiment, the carrier comprises a film forming material. In one embodiment, the carrier comprises a silicone adhesive. In one embodiment, the whitening agent is a peroxide compound.

Methods are also provided for making an oral care composition comprising:
 (a) mixing a whitening agent, silicone adhesive and carrier fluid to form a homogenous mixture;
 (b) adding a peroxide complex to said homogenous mixture, wherein said complex comprises hydrogen peroxide and an N-vinyl heterocyclic polymer; and
 (c) mixing under vacuum.

Methods are also provided for whitening a tooth surface, comprising applying a composition comprising a safe and effective amount of a peroxide complex and a whitening agent.

It has been discovered that compositions and methods of this invention afford advantages over oral care compositions among known in the art, including one or more of enhanced whitening efficacy, providing a higher available concentration of bleaching agent, tooth adherence in the presence of saliva without the use of a dental tray, and release of the bleaching agent over a period of time. Further uses, benefits and embodiments of the present invention are apparent from the description set forth herein.

DESCRIPTION

The following definitions and non-limiting guidelines must be considered in reviewing the description of this invention set forth herein. The headings (such as "Introduction" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As referred to herein, all compositional percentages are by weight of the total composition, unless otherwise specified.

Compositions

The present invention provides oral care compositions and methods for administration or application to, or use with, a human or other animal subject. As referred to herein, an "oral care composition" is any composition that is suitable for administration or application to the oral cavity a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative or cosmetic benefits; and combinations thereof. In various preferred embodiments, an oral care composition is not intentionally swallowed, but is rather retained in the oral cavity for a time sufficient to effect the intended utility. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio.

Peroxide Complex

The present invention provides compositions comprising a peroxide complex. The peroxide complex is preferably present at a level of from about 0.5% to about 40%, optionally from about 20% to about 30%. In a preferred embodiment, the concentration of the peroxide complex is such that the peroxide component of the peroxide complex is present at a level of about 10% of the total composition weight, optionally from about 1% to about 6% of the total composition weight.

The peroxide complex comprises a peroxide component and a porous cross-linked polymer. As referred to herein, a "peroxide component" is any oxidizing compound comprising a bivalent oxygen-oxygen group. Peroxide components include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as percarbonate and perborate salts of alkali and alkaline earth metals such as lithium, potassium, sodium, magnesium, calcium and barium, and mixtures thereof. In various embodiments, the peroxide component comprises hydrogen peroxide, urea peroxide, sodium percarbonate and mixtures thereof. In one embodiment, the peroxide component comprises hydrogen peroxide. In one embodiment, the peroxide component consists essentially of hydrogen peroxide.

The peroxide complex also comprises an N-vinyl heterocyclic polymer. Preferably, the polymer is crosslinked and adsorbs, absorbs, complexes, or otherwise retains the peroxide component. The chemical and physical characteristics of the particulate hinder the release of the peroxide compound from the polymer particulates, and in some embodiments provides controlled release of the peroxide compound. The peroxide complex preferably comprises a peroxide component at a level of from about 0.1% to about 25%, optionally from about 1% to about 25%, optionally from about 5% to about 18% by weight of the peroxide composite. In one embodiment, the composition comprises commercially available complex of peroxide adsorbed to cross-linked polyvinylpyrrollidone. Such products include, for example, Peroxydone XL-10 and Peroxydone K-30, marketed by ISP Corporation, Wayne, N.J., USA.

The N-vinyl heterocyclic polymer is derived from a N-heterocyclic vinyl monomer, preferably comprising N-vinyl heterocyclic monomers having from 3 to 7 atoms in a heterocyclic ring, including a carbonyl carbon atom and a nitrogen heteroatom containing a vinyl group. Preferably the ring contains 5 or 6 atoms, comprises heteroatoms such as sulfur or oxygen, and may be substituted or unsubstitued.

Certain embodiments are the polymers of specific N-vinyl heterocyclic monomers such as N-vinyl imides to form poly-N-vinyl polyimides, and N-vinyl lactams to form poly-N-vinyl polylactams, and mixtures thereof. Suitable N-vinyl imides include: N-vinyl malonimide; N-vinyl succinimide; N-vinyl glutarimide; N-vinyl maleimide; N-vinyl β-methyl-glutarimide; N-vinyl α-amylsuccinimide; and N-vinyl adipimide.

Suitable N-vinyl lactams include: N-vinyl peperidone; N-vinyl caprolactam; N-vinyl-3-methyl pyrrolidinone or piperidine, or caprolactam; N-vinyl-4-methyl pyrrolidinone, or piperidone or caprolactam; N-vinyl-5-methyl pyrrolidinone or piperidone; N-vinyl-3-ethyl pyrrolidinone; N-vinyl-4,5-dimethyl pyrrolidinone; N-vinyl-5,5-dimethyl pyrrolidinone; N-vinyl-3,3,5-trimethyl pyrrolidinone; N-vinyl-5-methyl-5-ethyl pyrrolidinone; N-vinyl-3,4,5-trimethyl-3-ethyl pyrrolidinone; N-vinyl-6-methyl-2-piperidone; N-vinyl-6-ethyl-2-piperidine; N-vinyl-3,5-dimethyl-2-piperidone; N-vinyl-4,4-dimethyl-2-piperidine; N-vinyl-7-methyl caprolactam; N-vinyl-7-ethyl caprolactam; N-vinyl-3,5-dimethyl caprolactam; N-vinyl-4,6-dimethyl caprolactam; N-vinyl-3,5,7-trimethyl caprolactam.

Embodiments containing poly-N-vinyl polylactams, include but are not limited to poly-N-vinyl pyrrolidone, poly-N-vinyl-2-piperidine, poly-N-vinyl-2-caprolactam, poly-N-vinyl-3-methyl-1-2-caprolacam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, and mixtures thereof. Preferably, the polymer is selected from the group consisting of poly-N-vinyl poly-2-pyrrolidone, poly-N-vinyl-poly-2-piperidone, poly-N-vinyl-poly-2-caprolactam and mixtures thereof.

In a preferred embodiment, the polymer is poly-N-vinyl-poly-2-pyrrolidone. The poly-N-vinyl-poly-2-pyrrolidone is also commonly known as polyvinylpyrrolidone or "PVP". PVP refers to a polymer containing vinylpyrrolidone (also referred to as N-vinylpyrrolidone, N-vinyl-2-pyrrolidione and N-vinyl-2-pyrrolidinone) as a monomeric unit. The monomeric unit, consists of a polar imide group, four non-polar methylene groups and a non-polar methane group. The polymers include soluble and insoluble homopolymeric PVPs. Copolymers containing PVP include vinylpyrrolidone/vinyl acetate (also known as Copolyvidone, Copolyvidonum or VP-VAc) and vinylpyrrolidone/dimethylaminoethylmethacrylate.

Soluble PVP polymers among those useful herein are known in the art, including Povidone, Polyvidone, Polyvidonum, poly (N-vinyl-2-pyrrolidinone), poly (N-vinylbutyrolactam), poly(1-vinyl-2-pyrrolidone) and poly [1-(2-oxo-1pyrrolidinyl)ethylene]. These PVP polymers are not substantially cross-linked.

In various embodiments of this invention, an insoluble cross-linked homopolymer is preferred. Such polymers include those commonly referred to in the art as polyvinylpolypyrrolidone, cross-povidone, and cPVP, and are referred to herein as "cPVP." The homopolymer is prepared by free radical polymerization of the monomer vinylpyrolidone.

In one embodiment, the poly-N-vinyl-poly-2-pyrrolidone has a lactam of the pyrrolidone ring that provides the hydrophilic characteristics. Without limiting the composition, mechanism, or function the invention, it is believed that such groups allow the peroxide compound to bind to the cPVP. The hydrophobic characteristics attributed to the methylene groups in the ring and the linear aliphatic backbone prevent the peroxide complex from reacting with saliva while still maintaining the peroxide available to whiten the teeth. The surface characteristic of the cPVP serve as a battier to the passage of the peroxide component and prevents the premature distribution of the peroxide component upon application of the oral care composition to the oral cavity. The cPVP linked peroxide is released over a period of time through diffusion, temperature variance, moisture levels and other factors.

Polymer particulates useful herein may be made by well established processes. The poly-N-vinyl polylactams are produced by polymerizing a vinyl lactam in the presence of an alkaline catalyst. (See, U.S. Pat. No. 2,938,017, Grosser, et al, issued May 24, 1960; U.S. Pat. No. 3,277,066, Grosser, et al, issued Oct. 4, 1966, and U.S. Pat. No. 3,306,886, Grosser, et al, issued Feb. 28, 1967). Embodiments containing poly-N-vinyl polyimides are produced by heating an N-vinyl imide in the presence of a catalyst. (See, U.S. Pat. No. 3,306,881, Grosser, et al, issued Feb. 8, 1967). In alternative embodiments comprising a co-polymer of the N-vinyl heterocyclic compound is produced by polymerizing N-vinyl heterocyclic and dissimilar vinyl monomers. (See U.S. Pat. No. 2,667,473, Morner, et al, issued Jan. 26, 1954; and U.S. Pat. No. 2,947,633, Peru et al, issued Aug. 2, 1960).

Porous cross-linked polymers among those useful herein include those commercially available as: Kollidon® and Luvicross®, marketed by BASF, Mount Olive, N.J., USA; PVP K-Series or Povidone K-30 marketed by AAA International Corp., Downers Grove, Ill., USA; PVP K-30 USP24 and industry grade, PVP VA-64, PVP K-17 and PVP K-90, marketed by Peakchem, Hangzhou, China; and Poly-Plasdone® INF-10, marketed by ISP Corporation, Wayne, N.J., USA. It is understood that embodiments of the invention are not limited to a PVP of a specific molecular weight and that any equivalent PVP of acceptable purity, preferably pharmaceutical grade, is within the scope of embodiments of this invention.

In various embodiments, the peroxide complex is made by suspending the polymer (preferably cPVP) in a suitable anhydrous organic solvent. An anhydrous solution of the peroxide component is made, preferably utilizing the same organic solvent as the PVP suspension. The peroxide solution is combined with the PVP suspension in an amount corresponding to the desired molar ratio of polymer peroxide of the peroxide complex. (See, U.S. Pat. No. 5,108,742, Merianos, issued Apr. 28, 1992; and U.S. Pat. No. 4,564, 514, Druaz, et al, issued Jan. 14, 1986.) In one embodiment, the peroxide complex has an equal (1:1) molar ratio of hydrogen peroxide to the polymer.

Whitening Agent

In various embodiments, the compositions of the present invention comprise a whitening agent. As further discussed below, a "whitening agent" is a material which is effective to effect whitening of a tooth surface to which it is applied. In various embodiments, the compositions of this invention comprise a peroxide whitening agent, comprising a peroxide compound. As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In one embodiment, the peroxide compound comprises hydrogen peroxide. In one embodiment, the peroxide compound consists essentially of hydrogen peroxide. The peroxide compound comprises from about 0.1% to about 50%, optionally from about 1% to about 40%, optionally from about 10% to about 30% of the oral care composition.

The peroxide compound may be the same as or different than the peroxide component. In one embodiment, the peroxide component and the peroxide compound are the same, both comprising hydrogen peroxide. The peroxide compound may be formulated in the composition as an aqueous solution. In one embodiment, the composition comprises an aqueous solution of hydrogen peroxide, comprising approximately 35% hydrogen peroxide in water.

In one embodiment, the concentration of the peroxide complex is limited so that the peroxide component is no more than 6%, so as to maintain an preferred viscosity. In such an embodiment, the combination of the peroxide complex and peroxide compound comprise a total peroxide concentration of greater than 6%, operable to provide more effective bleaching. Furthermore, in alternative embodiments where a peroxy acid serves as the peroxide compound, the oxidizing strength of the oral care composition is increased due to the leaving qualities of the $RCO_2$-component of the peroxy acid.

In various embodiments, the compositions comprise a non-peroxide whitening agent. Non-peroxide whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite.

The whitening agent preferably comprises from about 0.1% to about 20% of the oral care composition. In a preferred embodiment, the peroxide compound comprises from about 1% to about 10% of the oral care composition.

Orally Acceptable Carrier

The present invention provides compositions comprising an orally acceptable carrier. As used herein, an "orally acceptable carrier" refers to a material or combination of materials that are safe for use in the compositions of the present invention, commensurate with a reasonable benefit/risk ratio, with which the peroxide complex and whitening agent may be associated while retaining significant efficacy. Preferably, the carrier does not substantially reduce the efficacy of the peroxide complex or whitening agent. Selection of specific carrier components is dependant on the desired product form, including dentifrices, rinses, gels, and paints. In various embodiments, the carrier is operable to sufficiently adhere the peroxide complex against surfaces within the oral cavity to which the composition is administered, without concomitant use of a dental, tray, mouthpiece, tape, or similar appliance. In various embodiments, the carrier is operable for use with a tape, tray, mouthpiece or similar appliance.

Materials among those that are useful in carriers include adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier mrmaterials are selected for compatibility with the peroxide complex and with other ingredients of the composition.

In various embodiments, the carrier comprises an adhesion agent. As referred to herein, an adhesion agent is a material or combination of materials that enhance the retention of the peroxide complex on the oral cavity surface onto which the composition is applied. Such adhesion agents include adhesives, film forming materials, viscosity enhancers and combinations thereof. Such materials include hydrophilic organic polymers, hydrophobic organic polymers, silicone gums, silicone adhesives, silicas, and combinations thereof. Adhesion agents are preferably present at a level of from about 0.01% to about 75%, optionally from about 1% to about 40%. Accordingly, the present invention provides oral care compositions comprising:
  (a) a peroxide complex comprising hydrogen peroxide and an N-vinyl heterocyclic polymer;
  (b) whitening agent; and
  (c) an orally acceptable non-aqueous carrier.

Hydrophilic organic polymers useful herein include polyethylene glycols, nonionic polymers of ethylene oxide, block copolymers of ethylene oxide and propylene oxide, carboxymethy ene polymers, N-vinyl heterocyclic polymers, and mixtures thereof. Nonaqueous hydrophilic polymers useful in the practice of the present invention preferably provide a viscosity for the composition in the range between about 10,000 cps to 600,000 cps.

Hydrophilic polymers also include polymers of polyethylene glycols and ethylene oxide having the general formula:

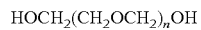

wherein n represents the average number of oxyethylene groups. Polyethylene glycols available from Dow Chemical (Midland, Mich., U.S.A.) are designated by number such as 200, 300, 400, 600, 2000 which represents the approximate average molecular weight of the polymer. Polyethylene glycols 200, 300, 400 and 600 are clear viscous liquids at room temperature, and are preferred for use in the practice of the present invention.

Another hydrophilic polymer useful herein is comprised of a water soluble, nonionic block copolymer of ethylene oxide and propylene oxide of the formula: $HO(C_2H_4O)_a(C_3H_6O)_b(C_2H_4O)_cH$. The block copolymer is preferably chosen (with respect to a, b and c) such that the ethylene oxide constituent comprises from about 65 to about 75% by weight, of said copolymer molecule and the copolymer has an average molecular weight of from about 2,000 to about 15,000, with the copolymer being present in oral care composition in such concentration that the composition is liquid at room temperature (23° C.).

A block copolymer useful herein is Pluraflo L1220 (marketed by BASF, Mount Olive, N.J., U.S.A.), which has an average molecular weight of about 9,800. The hydrophilic poly(ethylene oxide) block averages about 65% by weight of the polymer.

Organic polymers useful as adhesion enhancing agents include hydrophilic polymers such as carborners such as carboxymethylene polymers such as acrylic acid polymers, and acrylic acid copolymers. Carboxypolymethylene is a slightly acidic vinyl polymer with active carboxyl groups. One such carboxypolymethylene is Carbopol® 974 marketed by Noveon, Inc., Cleveland, Ohio, U.S.A.

In one embodiment, the compositions comprise an N-vinyl heterocyclic polymer in addition to the N-vinyl heterocyclic polymer that is a component of the peroxide complex. Such N-vinyl heterocyclic polymers include those discussed above. In one embodiment, the N-vinyl heterocyclic polymer is the same as that which is a component of the peroxide complex. In one embodiment, the N-vinyl heterocyclic polymer is different that that which is a component of the peroxide complex. In a preferred embodiment, the polymer is poly-N-vinyl-poly-2-pyrrolidone, preferably polyvinylpyrrolidone, cross-povidone, and cPVP Hydrophobic organic materials useful as adhesion enhancing agents in the practice of the present invention include hydrophobic materials such as waxes such as bees wax, mineral oil, mineral oil and polyethylene blends (Plastigel® marketed by Lyne Laboratories, Brockton, Mass., USA.), petrolatum, white petrolatum, liquid paraffin, butane/ethylene/styrene hydrogenated copolymer) blends (Versagel® marketed by Penreco, Houston, Tex., U.S.A.), acrylate and vinyl acetate polymers and copolymers, polyethylene waxes, silicone polymers as discussed further herein and polyvinyl pyrrolidone/vinyl acetate copolymers. In embodiments of the present invention containing a hydrophobic polymer, present in ratios of about 1 to about 85% weight of the composition.

Silicone polymers useful herein include, but are not limited to, silicone adhesives, silicone elastomers, silicone fluids, silicone resins, silicone gums and mixtures thereof. In one embodiment, the carrier comprises a pressure sensitive adhesive (PSA) composition, including those that are well known in the art. Generally, silicone based PSA's are produced by condensing a silicone resin and an organosiloxane such as a polydiorganosiloxane. Suitable silicone polymers include the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone pressure sensitive adhesive. A catalyst, for example an alkaline material such as ammonia, ammonium hydroxide or ammonium carbonate, can be mixed with the silanol-terminated polydiorganosiloxane and the silicone resin to promote this crosslinking reaction. Copolymerizing the silicone resin with the silanol terminated polydiorganosiloxane affords a self adhering and cohesive soft elastomer matrix. Modifying the silicone resin to polydiorganosiloxane ratio of the pressure sensitive adhesive will modify the tackiness of the oral care composition. For example PSAs are available from the Dow-Corning Corporation, Midland, Mich., U.S.A., under the brand name BIO-PSA. The silicone based pressure sensitive adhesive is present in the liquid whitening compositions of the present invention at a concentration of about 0.5% to about 99%, optionally from about 5% to about 60%, optionally from about 10% to about 40%.

Silicone gums useful herein include high molecular weight polydiorganosiloxanes having a viscosity at 25° C. of from about 500,000 cS up to about 50,000,000 cS. Such silicone gums include those polydiorganosiloxanes with an average molecular weight of greater than 500,000. The polysiloxane gums for use herein can be linear or cyclic, and branched or unbranched. Substituents may have any structure as long as the resulting polysiloxanes are hydrophobic, are not irritating, toxic or otherwise harmful when applied to the oral cavity, and are compatible with the other components of the composition. Specific examples of siloxane gums include polydimethylsiloxane, methylvinylsiloxane, copolymer, poly(dimethylsiloxane, diphenyl, methyvinylsiloxane) copolymer, and mixtures thereof. Silicone gums include those commercially available, such as SE30, marketed by General Electric.

Polysiloxane fluids useful herein include those with a viscosity, at 25° C., of from about 1 cS to about 1000 cS, preferably from about 2 cS to about 500 cS, and optionally from about 5 cS to about 400 cS. Polysiloxane fluids for use herein can be linear or cyclic, and can be substituted with a wide variety of substituents (including as described above). Preferred substituents include methyl, ehtyl and phenyl substituents. Suitable polysiloxane fluids include linear polysiloxane polymers such as dimethicone and other low viscosity analogues of the polysiloxane materials, preferably having a viscosity at 25° C. of 200 cS or less and cyclomethicone, and other cyclic siloxanes having for example a viscosity at 25° C. of 200 cS or less. Commercial examples of materials that are suitable for use herein include DC200 series fluids marketed by Dow-Corning Corporation and the AK Fluid series marketed by Wacker-Chemie GmbH, München, Germany.

Adhesion agents also include inorganic materials. Such inorganic materials include silicon polymers such as amorphous silica compounds which function as thickening agents (Cab-o-sil® fumed silica manufactured by Cabot Corporation, Boston, Mass., U.S.A.; and Sylox 15 also known as Sylodent 15, marketed by Davison Chemical Division of W. R. Grace & Co., Columbia, Md., U.S.A.).

Thickening agents among those useful herein include carboxyvinyl polymers, carrageenans (also known as Irish moss and more particularly iota-carrageenan), cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica, and mixtures thereof. One or more thickening agents are optionally present in a total amount of about 0.01% to about 15%, for example about 0.1% to about 10% or about 0.2% to about 5% by weight of the composition.

Viscosity modifiers among those useful herein include mineral oil, petrolatum, clays and organomodified clays, silica, and mixtures thereof. In various embodiments, such viscosity modifiers are operable to inhibit settling or separation of ingredients or to promote redispersibility upon agitation of a liquid composition. One or more viscosity modifiers are optionally present in a total amount of about 0.01% to about 10%, for example about 0.1% to about 5% by weight of the composition.

Diluents among those useful herein include materials or combinations of materials that are operable to solubilize and for suspend other components of the composition. In various embodiments, diluents are operable to adjust the viscosity of the composition, optionally in conjunction with viscosity modifiers (as discussed herein) and other components of the composition. The composition is preferably non-aqueous, i.e., does not contain appreciable amounts of chemically-unbound water in addition to water added consequent to the peroxide compound. Preferably, the composition comprises less than about 5% water in the carder. Diluents among those useful herein include glycerin and lower alcohols (e.g., $C_1$-$C_5$ alcohol., preferably ethanol). Diluents are present in the nonaqueous liquid whitening compositions of the present invention in amounts of about 0.1% to about 90%, optionally in various embodiments from about 0.5% to about 70%, from about 0.5% to about 50%, from about 0.5% to about 35%.

Surfactants among those useful herein include anionic, nonionic, and amphoteric surfactants. Surfactants may be used, for example, to provide enhanced stability of the formulation, to help in cleaning the oral cavity surfaces through detergency, and to provide foam upon agitation, e.g., during brushing with a dentifrice composition of the invention. Suitable anionic surfactants include water-soluble salts of $C_{8-20}$ alkyl sulfates, sulforiated monoglycerides $C_{8-20}$ fatty acids, sarc sinates, taurates, and mixtures thereof. Illustrative examples of these and other surfactants are sodium lauryl sulfate, sodium coconut monoglyceride sulfonate, sodium lauryl sarcosinate, sodium lauryl isoethionate, sodium laureth carboxylate and sodium dodecyl benzenesulfonate, and mixtures thereof. Suitable nonionic surfactants include xpoloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof. Suitable amphoteric surfactants include derivatives of $C_{8-20}$ aliphatic secondary and tertiary amines having an anionic group such as carboxylate, sulfate, sulfonate, phosphate or phosphonat. A suitable example is cocoamidopropylbetaine. One or more surfactants are optionally present in a total amount of about 0.01% to about 10%, for example about 0.05% to about 5% or about 0.1% to about 2%. Preferably, the surfactant is nonionic and compatible with peroxide compounds such as polyethylene oxide. Nonionic surfactants are present in embodiments of this invention at levels of from about 0.01% to about 1%.

Foam modulators useful herein include materials operable to increase amount, thickness or stability of foam generated by the composition (e.g., dentifrice compositions) upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. One or more PEGs are optionally present in a total amount of about 0.1% to about 10%, for example about 0.2% to about 5% or about 0.25% to about 2%.

Humectants useful herein include polyhydric alcohols such as glycerin, sorbitol, xylitol or low molecular weight PEGs. In various embodiments, humectants are operable to prevent hardening of paste or gel compositions upon exposure to air. In various embodiments humectants also function as sweeteners. One or more humectants are optionally present in a total amount of about 1% to about 50%, for example about 2% to about 25% or about 5% to about 15%.

Peroxide activators such as sodium bicarbonate, sodium carbonate, manganese gluconate may be incorporated in the compositions of the present invention. The activator is relatively nonactive with the peroxide whitening agent in nonaqueous liquid compositions. In various embodiments, the activator is operable to react with the peroxide to release oxygen when the liquid whitening composition applied to the teeth is contacted with saliva in the oral cavity. The peroxide activator is optionally present in embodiments of this invention at a concentration of about 0.1% to about 50%.

pH modifying agents among those useful herein include acidifying agents to lower pH, basifying agents to raise pH, and buffering agents to control pH within a desired range. For example, one or more compounds selected from acidifying, basifying and buffering agents can be included to provide a pH of about 2 to about 10, or in various embodiments from about 2 to about 8, from about 3 to about 9, from about 4 to about 8, from about 5 to about 7, from about 6 to bout 10, and from about 7 to about 9. Any orally acceptable pH modifying agent can be used, including carboxylic, phosphoric and sulfonic acids, acid salts (e.g., monosodium citrate, disodiu n citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole, and mixtures thereof. One or more pH modifying agents are optionally present in a total amount effective to maintain the composition in an orally acceptable pH range.

Mouth-feel agents include materials which impart a desirable texture or other feeling during use of the composition. Such agents include bicarbonate salts, which in various embodiments impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate, and mixtures thereof. One r more bicarbonate salts are optionally present in a total amount of 0.1% to about 50%, for example about 1% to about 20%.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include methol, menthyl acetate, menthyl lactate, camphor, eucalyptus oil, eucalyptol, anethole, eugenol, cassia, oxanone, α-irisone, propenyl guaiethol, thymol, linaloral, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5%, optionally from about 0.01% to about 1%.

Colorants among those useful herein include pigments, dyes, lakes and agents imparting a particular luster or reflectivity such as pearling agents. In various embodiments, colorants am operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

In one embodiment, the present invention provides compositions comprising:
  (a) from about 0.5% to about 60% of a peroxide complex
  (b) from about 0.5% to about 60% of a whitening agent; and
  (c) from about 0.5% to about 60% of a silicone adhesive.
Optionally, the composition additionally comprises from about 1 to about 99% of a silicone fluid. Optionally, the composition additionally comprises from about 1% to about 40% of a hydrophobic polymer, such as a blend of mineral oil and polyethylene glycol.

Optional Active Materials

The compositions of the present invention optionally comprise an active material, which is operable for the prevention or treatment of a condition or disorder of hard or soft tissue of the oral cavity, the prevention or treatment of a physiological disorder or condition, or to provide a cosmetic benefit. In various embodiments, the active is a "systemic active" which is operable to treat or prevent a disorder which, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives. Preferably, such actives are selected for compatibility with the peroxide complex, peroxide compound, and, other ingredients of the composition. Actives among those useful herein are disclosed in U.S. Patent Publication 2003/0206874, Doyle et al., published Nov. 6, 2003; U.S. Pat. No. 6,290,933, Durga et al., issued Sep. 18, 2001; and U.S. Pat. No. 6,685,921, Lawlor, issued Feb. 3, 2004.

Actives useful herein are optionally present in the compositions of the present invention in safe and effective amounts. A "safe and effective" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

The compositions of the present invention optionally comprise an abrasive. In various embodiments, an abrasive is useful for example as a polishing agent. Any orally acceptable abrasive can be used, but type, fineness (particle size) and amount of abrasive should be selected so that tooth enamel is not excessively abraded in normal use of the composition. Suitable abrasives include silica, for example in the form of silica gel, hydrated silica or precipitated silica, alumina, insoluble phosphates, calcium carbonate, resinous abrasives such as urea-formaldehyde condensation products, and mixtures thereof. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically about 5% to about 70%, for example about 10% to about 50% or about 15% to about 30% by weight of the composition. Average particle size of an abrasive, if present, is generally about 0.1 to about 30 μm, for example about 1 to about 20 μm or about 5 to about 15 μm.

The compositions of the present invention optionally comprise a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. One or more anticalculus agents are optionally present in an anticalculus effective total amount, typically about 0.01% to about 50%, for example about 0.05% to about 25% or about 0.1% to about 15%.

The compositions of the present invention optionally comprise fluoride ion source useful, for example, as an anti-caries agent. Any orally acceptable fluoride ion source can be used, including potassium, sodium and ammonium fluorides and monofluorophosphates, stannous fluoride, indium fluoride, and mixtures thereof. In various embodiments, water-soluble fluoride ion sources are used. One or more fluoride ion sources are optionally present in an amount providing a total of about 0.0025% to about 2%, for example about 0.005% to about 1% or about 0.01% to about 0.3%, of fluoride ions.

The compositions of the present invention optionally comprise a stannous ion source useful, for example, as a periodontal active, tartar control agent, anticaries agent or tooth desensitizer. Any orally acceptable stannous ion source can be used, including stannous fluoride, other stannous halides such as stannous chloride dihydrate, organic stannous carboxylate salts such as stannous formate, acetate, gluconate, lactate, tartrate, oxalate, malonate and citrate, stannous ethylene glyoxide, and mixtures thereof. One or more stannous ion sources are optionally present in a total amount of from about 0.01% to about 10%, optionally from about 0.1% to about 7% or from about 1% to about 5%.

The compositions of the present invention optionally comprise an antimicrobial (e.g., antibacterial) agent. Any orally acceptable antimicrobial agent can be used, including triclosan (5-chloro-2-(2,4-dichlorophenoxy)phenol); 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, and alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidine derivatives such as delmopinol and octapinol; magnolia extract; grapeseed extract; thymol; eugenol; menthol; geraniol; carvacrol; citral; eucalyptol; catechol; 4-allyicatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, e, al., issued Jul. 7, 1998.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a saliva stimulating agent, useful for example in amelioration of dry mouth. Any orally acceptable saliva stimulating agent can be used, including without limitation food acids such as citric, lactic, rilalic, succinic, ascorbic, adipic, fumaric and tartaric acids, and mixtures thereof. One or more saliva stimulating agents are optionally present in a saliva stimulating effective total amount.

The compositions of the present invention optionally comprise a breath freshening agent. Any orally acceptable breath freshening agent can be used, including without limitation zinc salts such as zinc gluconate, zinc citrate and zinc chlorite, α-ionone, and mixtures thereof. One or more breath freshening agents are optionally present in a breath freshening effective total amount.

The compositions of the present invention optionally comprise an antiplaque (e.g., plaque disrupting) agent. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates, and mixtures thereof.

The compositions of the present invention optionally comprise an anti-inflammatory agent. Any orally acceptable anti-inflammatory agent can be used, including steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone, and mixtures thereof.

The compositions of the present invention optionally comprise comprise an $H_2$ antagonist. $H_2$ antagonists useful herein include cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, IC1-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB408.4, and mixtures thereof.

The compositions of the present invention optionally comprise a desensitizing agent. Desensitizing agents useful herein include potassium citrate, potassium chloride, potassium tartrate, potassium bicarbonate, potassium oxalate, potassium nitrate, strontium salts, and mixtures thereof. Alternatively or in addition a local or systemic analgesic such as aspirin, codeine, acetaminophen, sodium salicylate or triethanolamine salicylate can be used.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropies (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

The compositions of the present invention optionally comprise proteins. Suitable proteins include milk proteins and enzymes such as peroxide-producing enzymes, amylase, plaque-disrupting agents such as papain, glucoamylase, glucose oxidase, and "next generation" enzymes."

Methods of Manufacture

The liquid whitening compositions of the present invention are made by any of a variety of methods, including adding and mixing the ingredients of the composition in a suitable vessel such as a stainless steel tank provided with a mixer. In one embodiment, a whitening agent, silicone adhesive and carrier fluid are mixed to form a homogenous mixture. The peroxide complex is then added to the homogenous mixture and the newly formed composition is mixed under a vacuum. In one embodiment, the liquid ingredients are combined (e.g., in the order of whitening agent such as liquid hydrogen peroxide, silicone fluid, silicone adhesive fluid and Pluracare), and mixed at high speed for 30 minutes. Plastigel (if present) is then added and the solution is mixed at high speed for five minutes. Finally, the peroxide complex is added and the composition is mixed at high speed for fifteen minutes under vacuum. Additional ingredients such as flavorant, coloring or sweeteners are added at any point during the mixing process but in various embodiments such ingredients are preferably added last or close to last. In some embodiments, the peroxide complex is formed in situ, such that the method comprises mixing a peroxide component (e.g., solution of hydrogen peroxide) and N-vinyl heterocyclic polymer (e.g., cPVP), with an additional quantity of peroxide compound. In other embodiments, the peroxide complex is formed prior to addition to the remainder of the composition.

Methods

The present invention provides methods for whitening a tooth surface using compositions according to the present invention. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity. As used herein, "whitening" refers to a change in visual appearance of a tooth, preferably such that such that the tooth has a brighter shade.

Increase in whiteness of a dental surface can be observed visually, for example with the aid of color comparison charts or gauges, or measured by colorimetry, using any suitable instrument such as a Minolta Chro eter, e.g., model CR-400 (Minolta Corp., Ramsey, N.J.). The instrument can be programmed, for example, to measure Hunter Lab values or L*a*b* values according to the standard established by the International Committee of Illumination (CIE). The L*a*b* system provides a numerical representation of three-dimensional color space where L* represents a lightness axis, a* represents a red-green axis and b* represents a yellow-blue axis. The L* and b* axes are typically of greatest applicability to measurement of tooth whiteness. Increase in whiteness can be computed from differences in L*, a* and b* values before and after treatment, or between untreated and treated surfaces. A useful parameter is $\Delta E^*$, calculated as the square root of the sum of the squares of differences in L*, a* and b* values, using the formula:

$$\Delta E^* = [(\Delta L^*)2 + (\Delta a^*)2 + 9\Delta b^*)2]1/2$$

A higher value of $\Delta E^*$ indicates greater increase in whiteness. In various embodiments, the method of the present invention can effect a $\Delta E^*$ of at least about 1, or at least about 3, or at least about 4, or at least about 5.

Accordingly, the present invention provides methods for whitening a tooth surface, comprising applying to the surface a safe and effective amount of a mixture of a peroxide complex comprising a peroxide compound and a porous cross-linked polymer and a whitening agent. Preferably the method comprises applying a composition of the present invention, comprising the peroxide complex, whitening agent, and a carrier. As referred to herein, "applying" refers to any method by which the peroxide complex is placed in contact with the tooth surface. Such methods, in various embodiments, comprise direct application of a composition by such methods as rinsing, painting, and brushing. In various embodiments, application of the composition comprises the use of an application device which aids in maintaining contact of the composite to the tooth surface for sufficient time so as to allow whitening.

Suitable application devices include dental trays, mouthpieces, floss, fibers, chips, strips and tapes. Strips among those useful herein comprise polymers, natural and synthetic woven materials, non-woven material, foil, paper, rubber and combinations thereof. Preferably the strip of material is substantially water insoluble. Suitable polymers include polyethylene, ethylvinylacetate, polyesters, ethylvinyl alcohol, fluoroplastics, and combinations thereof In various embodiments, the strip of material is generally less than about 1 mm (millimeter) thick, optionally less than about 0.05 mm thick, optionally about 0.001 to about 0.03 mm thick. The shape of the strip is any shape and size that covers the desired oral surface. In one embodiment, the length of the strip material is from about 2 cm (centimeter) to about 12 cm, in another embodiment from about 4 cm to about 9 cm. The width of the strip material will also depend on the oral surface area to be covered. The width of the strip is generally from about 0.5 cm to about 4 cm, in one embodiment from about 1 cm to about 2 cm. The strip material may comprise shallow pockets, optionally filled by a composition of this invention so as to provide reservoirs of peroxide complex. Strips among those useful herein are disclosed in U.S. Pat. No. 6,514,484, Rajaiah et al. issued Feb. 4, 2003.

In one preferred embodiment, the whitening composition is applied using a "paint on" technique. A small application device, such as a brush or spatula is coated with a composition of this invention and the composition is then placed on a tooth surface. Preferably, the composition be spread evenly on such surfaces, in sufficient quantity to deliver a whitening amount of peroxide complex.

The present invention also provides methods for effecting the controlled release of an oxidizing peroxide species onto a tooth surface, comprising contacting the surface with a mixture of a peroxide complex and whitening agent of the present invention. As referred to herein, such controlled release in various embodiments comprises release of the peroxide over a time sufficient to effect whitening of the teeth. Without limiting the mechanism, function or utility of present invention, in some embodiments contact with saliva causes the release of an effective amount of peroxide active from the cross-linked polymer matrix to the applied tooth site over a period of time. Preferably, the composition is contacted with the tooth surface for at least about 30 seconds, optionally at least about 1 minute.

In various embodiments, it is preferred that the subject does not eat or drink while the composition is in contact with the dental surface. The whitening composition can be removed as and when required, at will, by an employment of standard oral hygiene procedures such as brushing or by rinsing, e.g., with a mouthwash. The process can be repeated several times until the desired whitening results are achieved.

In various embodiments, compositions of the present invention are also used for the treatment or prevention of disorders in the oral cavity, including cavity prevention, whitening, plaque prevention or reduction, gingivitis prevention or reduction, tartar control, sensitivity prevention or reduction, breath malodor prevention or reduction, and stain prevention. Compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality. Such methods include, those disclosed in U.S. Patent Publication 2003/0206874, Doyle et al., published Nov. 6, 2003.

The present invention is further illustrated through the following non-limiting examples.

Example 1

A composition of the present invention is made, as follows:

| Ingredients | Weight % |
| --- | --- |
| cPVP-$H_2O_2$ powder | 25 |
| 35% Hydrogen Peroxide aqueous solution | 4 |
| DC Silicone Fluid—350 CST (Dimethylsiloxane) | 20 |
| DC 8-7016 Fluid (Silicone Adhesive) | 30 |
| Plastigel 5 | 20.1 |
| Sodium Saccharin | 0.3 |
| Mint Flavor | 0.6 |
| Total (%) | 100 |

The liquid hydrogen peroxide, DC silicone fluid, and silicone adhesive are combined and mixed at high speed for 30 minutes. The Plastigel is then added and the solution is mixed at high speed for five minutes. Finally, the peroxide complex, flavorant and sweetener are added and the composition is mixed at high speed for 20 minutes under vacuum until the composition is homogenous.

The composition is applied to the teeth of a human subject having stained teeth, resulting in perceptible whitening.

Example 2

A composition of the present invention is made, as follows:

| Ingredients | Weight % |
| --- | --- |
| cPVP-$H_2O_2$ powder | 10 |
| sodium percarbonate | 25 |
| DC Silicone Fluid—350 CST (Dimethylsiloxane) | 16.55 |
| DC 8-7016 Fluid (Silicone Adhesive) | 30 |
| Pluracare L-1220 | 1 |
| Plastigel 5 | 16.55 |
| sodium saccharin | 0.3 |
| mint flavor | 0.6 |
| Total (%) | 100 |

The composition is made by a process generally as described above in Example 1.

Example 3

A compositions of the present invention is made as follows.

| Ingredients | Weight % |
| --- | --- |
| cPVP-$H_2O_2$ powder | 25 |
| 35% hydrogen oxide | 12.14 |
| DC Silicone Fluid—350 CST (Dimethylsiloxane) | 15.96 |
| DC 8-7016 Fluid (Silicone Adhesive) | 30 |
| sodium saccharin | 0.3 |
| Pluracare L-1220 | 1 |
| Plastigel 5 | 15 |
| mint flavor | 0.6 |
| Total (%) | 100 |

The composition is made by a process generally as described above in Example 1, The composition is subjected to accelerated aging conditions (105° F./120° F.) for several weeks, and remains stable with more than 90% of the peroxide remaining.

The whitening efficacy of the composition is determined using a duplicate pair of flow cells designed to accommodate a total of eight bovine enamel blocks (four in each cell). The bovine enamel blocks are obtained freshly stained using an established staining protocol (Indiana University, Indianapolis, Ind.). The initial L*, a* and b* values are matched as closely as possible prior to an experiment using a chronometer (Minolta CR-321) based on initial L*, a* and b* values (CIELAB). These initial values are typically L*=25.00, a*=3.00, and b*=5.00 to L*=35.00, a*=5.00, and b*=7.00. The L, a, b values are measured four times at slightly differing locations on the surface of the bovine enamel blocks.

To simulate the saliva of the human mouth, an artificial saliva buffer solution maintained at 37° C. is prepared which contains the salts usually present in saliva at levels typical to the levels found in human saliva. The bovine enamel blocks are placed in the flow cells and the compositions evenly applied using a brush, the amount of product applied is determined using the weight difference of the container. Flow over the teeth is 0.6 ml/min. for 30 min. Average initial and final chromometer readings is used to calculate $\Delta E$ according to $\Delta E=((L_f-L_i)^2+(b_f-b_i)^2+(a_f-a_i)^2)^{1/2}$. The results of the tests, set forth in the following table, show that the composition has a whitening effect.

| ΔL | Δb | ΔE |
|---|---|---|
| 12.7 ± 1.7 | −5.7 ± 1.4 | 14 ± 2.1 |

What is claimed is:

1. An oral care composition comprising:
 (a) a peroxide complex; and
 (b) an orally acceptable carrier.

2. The composition of claim 1, wherein the orally acceptable carrier comprises a phosphate or a polyphosphate.

3. The composition of claim 2, wherein the phosphate or polyphosphate is selected from: monobasic, dibasic, tribasic sodium phosphates, sodium tripolyphosphate; tetrapolyphosphate; mono-, di-, tri- and tetrasodium pyrophosphates; sodium trimetaphosphate, sodium hexametaphosphate; and mixtures thereof.

4. The composition of claim 3, wherein the polyphosphate is selected from sodium tripolyphosphate and sodium hexametaphosphate.

5. The composition of claim 1, wherein the peroxide complex comprises a cross-linked polyvinyl pyrrolidone and hydrogen peroxide.

6. The composition of claim 1, wherein the orally acceptable carrier comprises a block copolymer of ethylene oxide and propylene oxide.

7. The composition of claim 1, wherein the peroxide complex is present at a level of 0.5% to 40% by weight of the total composition.

8. The composition of claim 7, wherein the peroxide complex is present at a level of 20% to 30% by weight of the total composition.

9. The composition of claim 1, further comprising a zinc ion source.

10. The composition of claim 1, wherein the composition is in the form of a toothpaste, mouthwash, a gel, and a strip.

11. The composition of claim 1, wherein the composition further comprises an enzyme.

12. The composition of claim 11, wherein the enzyme is a peroxide-producing enzyme.

\* \* \* \* \*

UNITED STATES PATENT AND TRADEMARK OFFICE
CERTIFICATE OF CORRECTION

PATENT NO. : 10,758,472 B2
APPLICATION NO. : 15/900346
DATED : September 1, 2020
INVENTOR(S) : Lynette Zaidel et al.

It is certified that error appears in the above-identified patent and that said Letters Patent is hereby corrected as shown below:

On the Title Page

In "Primary Examiner", delete "Banjamin" and insert -- Benjamin --, therefor.

On Page 2, item (56), under "OTHER PUBLICATIONS", Line 4, delete "multifuntional" and insert -- multifunctional --, therefor.

In the Specification

In Column 1, Line 22, delete "Without" and insert -- without --, therefor.

In Column 1, Line 38, delete "off-whim" and insert -- off-white --, therefor.

In Column 5, Line 22, delete "piperidine," and insert -- piperidone, --, therefor.

In Column 5, Line 29, delete "piperidine;" and insert -- piperidone; --, therefor.

In Column 5, Line 36, delete "piperidine," and insert -- piperidone, --, therefor.

In Column 6, Line 33, delete "Peru" and insert -- Perry --, therefor.

In Column 8, Line 27, delete "mrmaterials" and insert -- materials --, therefor.

In Column 11, Line 21, delete "carder." and insert -- carrier. --, therefor.

In Column 11, Line 36, delete "sulforiated" and insert -- sulfonated --, therefor.

In Column 11, Line 37, delete "sarc sinates," and insert -- sarcosinates, --, therefor.

In Column 12, Line 30, delete "bout" and insert -- about --, therefor.

Signed and Sealed this
Third Day of November, 2020

Andrei Iancu
*Director of the United States Patent and Trademark Office*

CERTIFICATE OF CORRECTION (continued)
U.S. Pat. No. 10,758,472 B2

In Column 12, Line 33, delete "disodiu n" and insert -- disodium --, therefor.

In Column 13, Line 31, delete "am" and insert -- are --, therefor.

In Column 15, Line 18, after "comprise", insert -- a --.

In Column 15, Line 58, delete "piperidine" and insert -- piperidino --, therefor.

In Column 15, Line 61, delete "4-allyicatechol;" and insert -- 4-allylcatechol; --, therefor.

In Column 16, Line 11, delete "rilalic," and insert -- malic, --, therefor.

In Column 17, Line 55, delete "Chro eter," and insert -- Chromameter, --, therefor.